United States Patent [19]
Jones et al.

[11] 3,981,178
[45] Sept. 21, 1976

[54] GAS DENSITY DETECTING APPARATUS

[75] Inventors: Lloyd R. Jones, Fairfield, Conn.;
Frederick W. Roberts, deceased, late of Southport, Conn., by Dorothy A. Roberts, executrix

[73] Assignee: Rolock Incorporated, Fairfield, Conn.

[22] Filed: Apr. 11, 1974

[21] Appl. No.: 460,045

Related U.S. Application Data

[63] Continuation of Ser. No. 298,510, Oct. 18, 1972, abandoned.

[52] U.S. Cl. ................................................ 73/30
[51] Int. Cl.² .................................... G01N 9/30
[58] Field of Search ............................ 73/30, 32 R

[56] References Cited
UNITED STATES PATENTS

1,133,556 3/1915 Gerdien ................................ 73/30

FOREIGN PATENTS OR APPLICATIONS

154,529 11/1921 United Kingdom .................... 73/523

Primary Examiner—Herbert Goldstein
Assistant Examiner—Anthony V. Ciarlante
Attorney, Agent, or Firm—Smythe & Moore

[57] ABSTRACT

There is disclosed an apparatus and process for detecting changes in the density of a gas wherein the gas to be measured is introduced into a closed casing at the rotary axis of a hollow disc wheel rotating within the casing. The disc wheel is provided with a plurality of radial vanes and the gas is centrifuged by the rotating disc. A Pitot tube positioned at the periphery of the disc measures the force exerted by the centrifuged gas to ascertain its mass which is then compared with a reference pressure.

3 Claims, 3 Drawing Figures

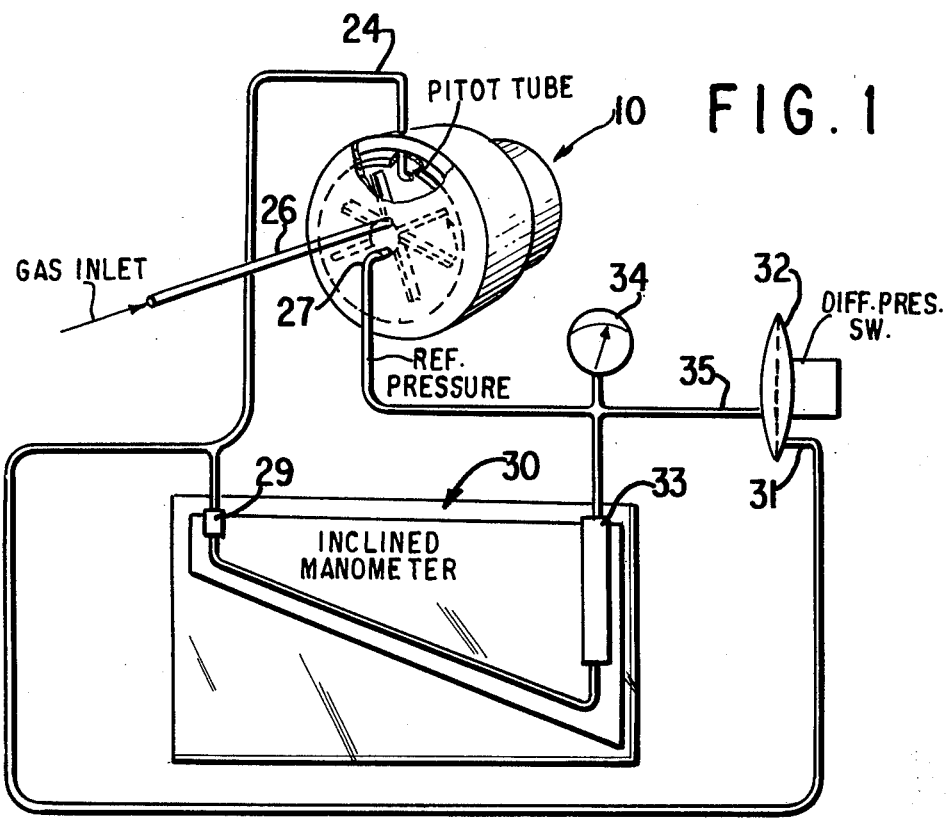
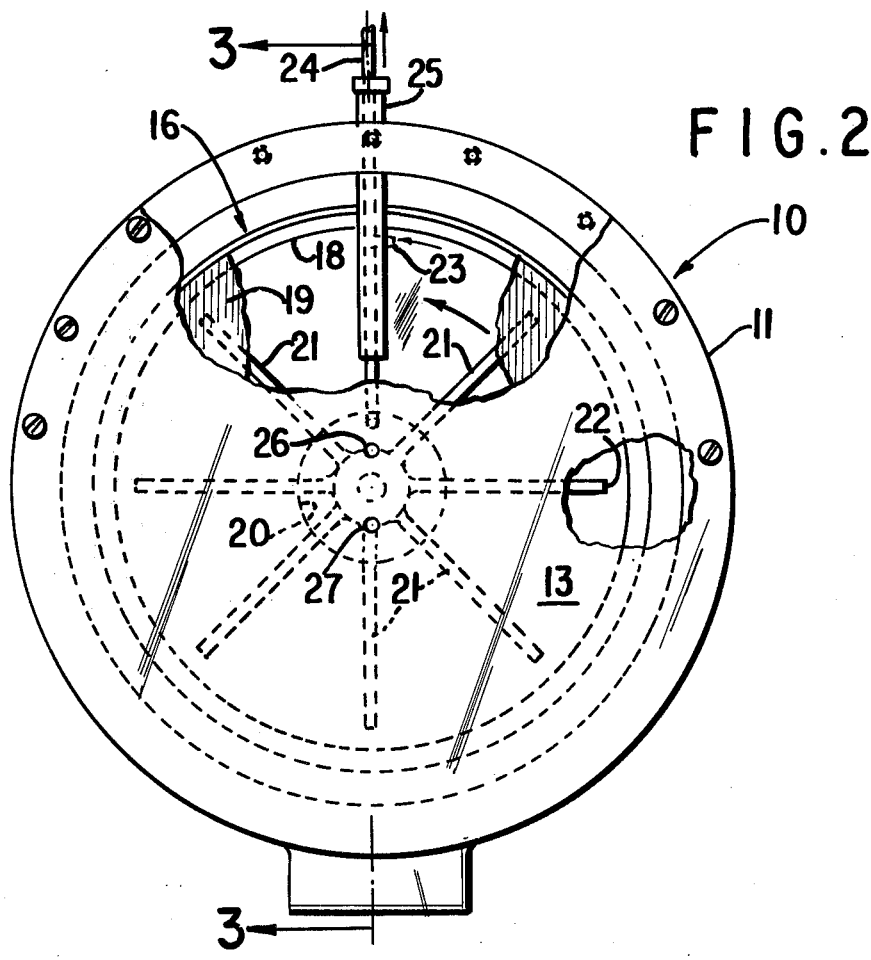

GAS DENSITY DETECTING APPARATUS

This is a continuation of application Ser. No. 298,510, filed Oct. 18, 1972, now abandoned.

This invention relates to detecting changes in density of a gas and, more particularly, to an apparatus and process for determining changes in the composition of natural gas supplied by the gas producer.

Natural gases have been widely used as fuels both by home owners and others for heating purposes and for various industrial processes, such as heat treating. In the colder areas of the United States and Canada, many of the natural gas pipe lines are unable to meet peak demands during the winter months. In order to satisfy the demands during these peak periods, individual gas companies add a mixture of propane and air to the natural gas drawn from the pipe line. This process is known as "peak-shaving." Propane alone cannot be added because the heat value of propane per cubic foot is more than twice that of natural gas. Accordingly, the propane normally is diluted with air in approximately the proportions of one part air to one part propane. However, the exact proportion varies from one company to another.

The domestic user or home owner using this gas for heating is not bothered by the increased heat value. However, industrial plants that use the gas as a raw material in heat treatment processes, rather than as a fuel, can be seriously affected unless it is precisely known when the peak-shaved gas arrives and departs from their plants. Also, the extent of the peak-shaving must be known.

Because the hydrogen-to-carbon ratio of methane is four to one, while the hydrogen-to-carbon ratio of propane is two and two-thirds to one, the resulting endothermic gas contains a higher percentage of carbon monoxide and a lower percentage of hydrogen during period of peak-shaving. Since the carbon potential in the furnace is a function of the square of the carbon monoxide divided by the first order of the carbon dioxide, the quality of work being carburized may be greatly affected by peak-shaving.

Many gas companies cooperate with heat treatment plants by advising when the peak-shaving is to start and even the extent of the peak-shaving. However, not all companies can tell the extent of the peak-shaving since it will vary with gas demands and may change from hour to hour. Such a telephone communication procedure has numerous disadvantages which are that the gas companies may either forget to call or may call at an hour when no one is at the plant to receive the call. Further, the gas companies seldom call when the peak-shaving process is stopped and when they do call, the time for the change back to the natural gas is as variable as the arrival time described above. Also, the time required for the peak-shaved gas to reach the plant of the heat treaters varies considerably with the demand and configuration of the gas main loops in the area served by the gas company. Finally, peak-shaving is usually discontinued in the evening hours when it may be difficult to make changes in the heat treatment process because few operating personnel are present at this time.

Various means have been suggested to analyze gas mixtures, such as seen in U.S. Pat. Nos. 1,133,556 and 2,035,039, but these have not been completely satisfactory.

One of the objects of the present invention is to provide an apparatus and process for quickly and accurately detecting peak-shaved gas.

Another object of the present invention is to provide an apparatus and process for detecting changes in the density of a gas.

According to one aspect of the present invention, a gas density detecting apparatus may comprise a centrifuging wheel rotating within a casing. Means are provided for rotating the wheel, and means are also provided for introducing the gas to be measured into the casing at a point adjacent the rotary axis of the wheel. A reference pressure, which may be a reference gas, is established in the vicinity of the centrifuging wheel. Means for sensing the mass of the centrifuged gas are provided in order to indicate the density of the measured gas. The sensing means may comprise a Pitot tube positioned tangentially at the perimeter of the centrifuging wheel and will measure ram and velocity of the gas.

The process of the present invention may comprise centrifuging the gas to be measured, sensing the mass of the centrifuged gas, and then comparing the sensed mass of the centrifuged gas with a reference pressure.

Other objects, advantages and features of the present invention will become apparent from the accompanying description and drawings, which are merely exemplary.

In the drawings:

FIG. 1 is an overall schematic representation of the gas density detecting apparatus according to the present invention;

FIG. 2 is an enlarged front elevational view of the detecting apparatus with a portion of the front wall removed to show the vane structure on the centrifuging wheel.

Proceeding next to the drawings wherein like reference symbols indicate the same parts throughout the various views, a specific embodiment of the present invention will be described in detail.

Figure 3:
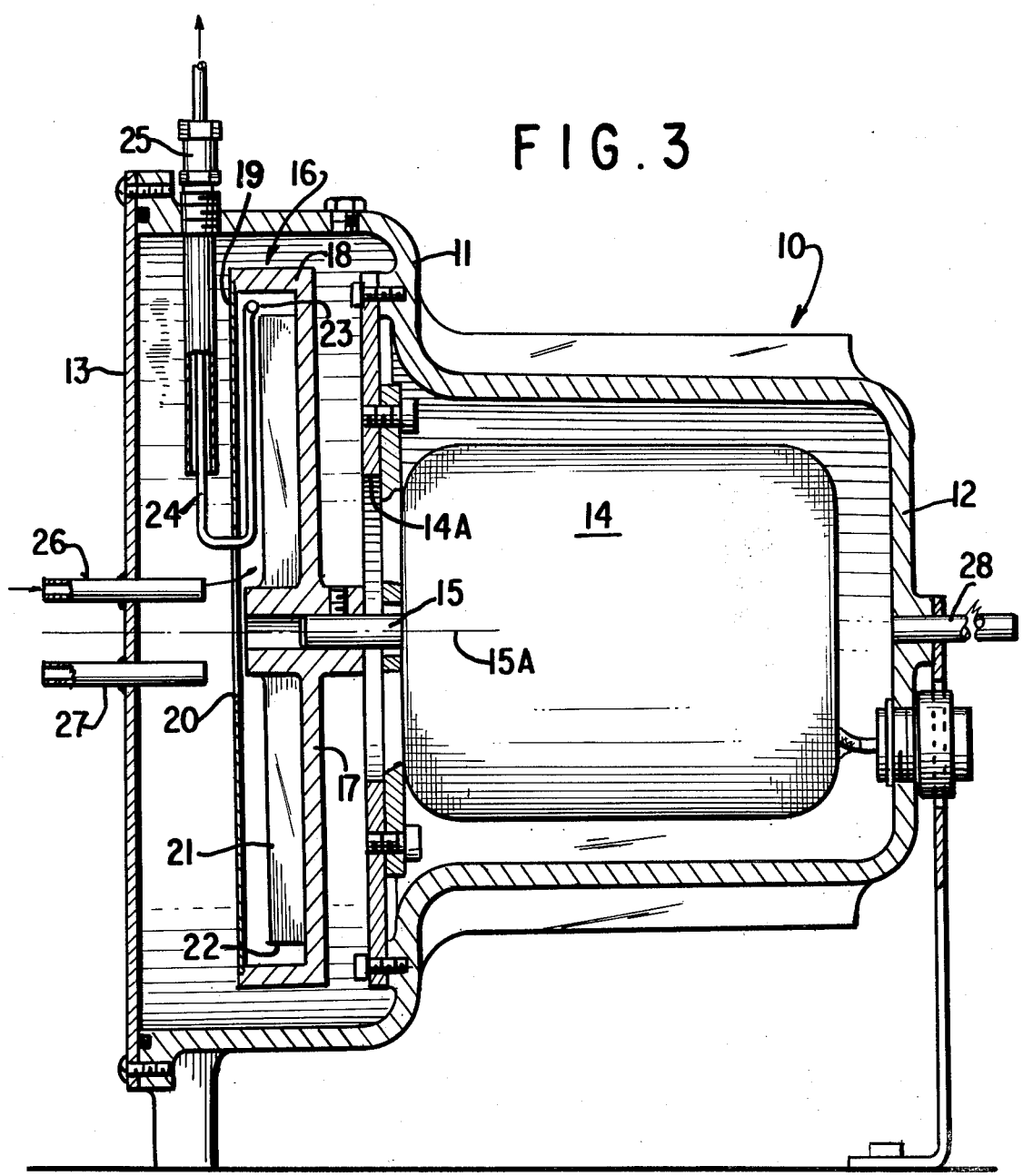
FIG. 3 is a longitudinal sectional view taken along the line 3—3 of FIG. 2.

As may be seen in the drawings, more particularly in FIGS. 2 and 3, the gas density analyzer of the present invention is indicated generally at 10 and comprises a substantially cylindrical casing 11 having a closed rear end 12 and a cover plate 13 closing the front end thereof. Mounted within the casing is an electric motor 14 having an output shaft 15 upon which is mounted a centrifuging wheel 16. The motor 14 may be of the hysteresis synchronous type so as to rotate at a constant synchronous speed. The centrifuging wheel 16 comprises a hollow disc having a rear wall 17 and peripheral wall 18 with a front wall 19 being mounted on the front edge of the peripheral wall 18. The front wall 19 is provided with a central opening 20.

The centrifuging wheel 16 is provided with a plurality of radially extending vanes 21 whose outer ends 22 terminate at points inwardly of the peripheral side wall 18.

A Pitot tube 23 is mounted tangentially relative to the outer ends of the vanes and will sense ram and velocity of the centrifuged gas. The tube 23 is connected to tube 24 which passes downwardly and outwardly through the central opening 20 and then outwardly of the casing through seal 25. By so locating the tube in the wheel, the tube will not be responsive to the shearing action at the front face of the vanes as the wheel rotates.

The gas to be measured is introduced through inlet 26 to a point adjacent the rotary axis 15 of the centrifuging wheel.

Also, a reference pressure is sensed at 27 at a point adjacent to the rotary axis of the wheel which serves to provide a reference pressure. The radial distance from the center or axis 15A of the entrances of tubes 26 and 27 is made equal.

Gas can be discharged from the casing through discharge tube 28 mounted in the rear wheel in the rear wall 12 of the casing so as to cool the motor which is in the enclosed casing. Also, apertures could be located in motor mounting wall 14A.

As can be seen in FIG. 1, the Pitot tube line 24 is connected to one end 29 of an inclined manometer 30. The line 24 also can be connected at 31 to a differential pressure switch 32 which may be employed to actuate signal lights and/or audible alarms.

The reference pressure in line 27 is connected to the other end 33 of the inclined manometer 30, to a pressure gauge 34 and to the other side at 35 of the differential pressure switch 32. The gas to be measured and reference gas are located at points spaced radially equal relative to the center of wheel 16.

The operation of the gas density analyzer according to the present invention is on the principle that peak-shaved gas is more dense than natural gas. The natural gas, the density of which is to be measured, is introduced into the apparatus through line 26. This gas is then centrifuged by rotating centrifuging wheel 16, and the pressure of the centrifuged gas is measured by a stationary probe in the form of Pitot tube 23. The pressure, proportional to the mass of the gas, is indicated by a sensitive and accurate inclined manometer 30. The measured pressure is also transmitted to the adjustable pressure sensitive switch 32 which may be set to light an alarm switch and send an audible alarm, if desired. The switch may be set to signal peak-shaving levels as low as 10 percent. It should be noted that gas companies generally operate at a 20 percent to 50 percent level when they commence peak-shaving. Upon receiving the signal, the heat treater can commence appropriate adjustment measures to, for example, either his generator or furnace dew points or carbon-dioxide level.

The reference pressure within the casing serves as a standard to indicate the precise degree of the peak-shaving. A reading of the manometer will indicate the degree of peak-shaving, and reference to a suitable chart will then indicate the correction necessary. A chart can be compiled for each gas density detecting apparatus for use a guide in resetting the generator and furnace dew points and levels of carbon dioxide during peak-shaving periods.

The apparatus of the present invention is particularly advantageous since no rotating seals are employed and no significant viscosity effects are present since the gas to be measured does not drive any wheel or other element. The gas is merely centrifuged within the hollow rotor or wheel. Thus, the present apparatus is responsive only to the mass of the gas being measured.

It will be understood that various details of construction and arrangement of parts and use of the invention may be made without departing from the spirit of the invention except as defined in the appended claims.

What is claimed is:

1. In a gas density detecting apparatus for measuring the density of a gas flowing through a conduit, the combination of a single casing, a rotatable centrifuging wheel located within said casing, said wheel being a hollow disc with a back face and a peripheral wall extending therefrom, said back face having a plurality of radially extending vanes thereon, said vanes terminating before said peripheral wall so as to provide a circumferential space therebetween, means for rotating said wheel, a front face on said hollow disc having central aperture means, inlet means for introducing the gas to be measured adjacent the rotary axis of said wheel, said gas being centrifuged outwardly in said hollow disc toward said peripheral wall and moving with said disc, means adjacent the rotary axis of said wheel for establishing a reference pressure within said casing, means for sensing the relative pressure of the centrifuged gas as compared with said reference pressure, said sensing means including a Pitot tube having its entrance orifice tangentially located adjacent the peripheral wall of said wheel and the ends of said vanes, so that the centrifuged gas provides ram and velocity effect in said Pitot tube, and outlet means thereby providing a gas flow path through said apparatus.

2. In a gas density detecting apparatus as claimed in claim 1 wherein the gas to be measured is introduced relative to the rotary axis of the wheel radially equidistant from said axis relative to the point where said reference pressure is established.

3. In a gas density detecting apparatus as claimed in claim 1 wherein said means for rotating said wheel is in said casing and including means on the casing for discharging gas therefrom past said means for rotating said wheel so as to cool said means for rotating said wheel.

* * * * *